United States Patent
Zylka et al.

(10) Patent No.: US 6,471,399 B1
(45) Date of Patent: Oct. 29, 2002

(54) X-RAY EXAMINATION DEVICE AND METHOD FOR PRODUCING UNDISTORTED X-RAY IMAGES

(75) Inventors: Waldermar Zylka, Hamburg (DE); Jorg Sabczynski, Norderstedt (DE); Jürgen Weese, Henstedt-Ulzburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/601,894
(22) PCT Filed: Jun. 15, 2000
(86) PCT No.: PCT/EP99/09225
§ 371 (c)(1), (2), (4) Date: Aug. 8, 2000
(87) PCT Pub. No.: WO00/33739
PCT Pub. Date: Jun. 15, 2000

(30) Foreign Application Priority Data

Dec. 8, 1998 (DE) .......................................... 198 56 537

(51) Int. Cl.$^7$ .............................................. G01D 18/00
(52) U.S. Cl. ................................ 378/207; 378/65; 378/4
(58) Field of Search .............................. 378/207, 65, 4, 378/62, 164

(56) References Cited

U.S. PATENT DOCUMENTS

| 4,233,507 A | * 11/1980 | Volz .............................. 250/252 |
| 5,675,380 A | * 10/1997 | Florent et al. ............... 348/251 |
| 5,748,768 A | *  5/1998 | Sivers et al. ................. 382/130 |
| 5,772,594 A |    6/1998 | Barrick ........................ 600/407 |
| 5,793,835 A | *  8/1998 | Blanck ........................... 378/4 |

\* cited by examiner

Primary Examiner—Robert H. Kim
Assistant Examiner—Irakli Kiknadze
(74) Attorney, Agent, or Firm—John Vodopia

(57) ABSTRACT

In an X-ray examination device and a method for generating distortion-free X-ray images the imaging properties are calculated and distortions are corrected by providing at least one calibration member (7, 8) for forming a reference pattern; a correction unit (13) corrects the distortions in X-ray images on the basis of the pattern of the calibration members (7, 8) actually formed in the patient X-ray image (FIG. 4) and the calculated reference pattern.

6 Claims, 2 Drawing Sheets

X-RAY EXAMINATION DEVICE AND METHOD FOR PRODUCING UNDISTORTED X-RAY IMAGES

BACKGROUND OF THE INVENTION

The invention relates to an X-ray examination apparatus for and a method of forming distortion-free X-ray images.

Mobile X-ray examination systems, for example C-arm X-ray systems, are used for given surgical interventions, for example for orthopedic surgery. Because of the mobile components of such an X-ray examination system and the continuously changing exposure circumstances, the X-ray images must be checked regularly for distortions. Methods and devices of this kind are also used for computer-aided surgery.

U.S. Pat. No. 5,772,594 describes a C-arm X-ray system in which a plurality of reference sensors are mounted on the image intensifier, said reference sensors being localized by a position measuring system. The bone to be treated is provided with markers which are localized by said position measuring system. In this X-ray system the image formed is displayed by means of an image processing device and the surgical tools of the surgeon, also being provided with sensors, are localized by the position measuring system and reproduced in the displayed X-ray image of the relevant bone. Changes of the position of the bone which occur during the operation and after the formation of the image are not reproduced.

Images produced by C-arm X-ray examination systems are usually distorted. Such distortions are due on the one hand to the curved surface of the image intensifier and on the other hand to changes of the external magnetic field, for example the terrestrial magnetic field. Moreover, for example, the C-arm is subject to bending due to the weight of the image intensifier and the X-ray source, said bending not being constant. Such bending and distortions lead to changes in the imaging properties and hence to X-ray images containing defects. Mobile C-arms can be moved to a different position or into a different orientation by the surgeon at any time, so that the imaging properties change continuously.

For novel surgical techniques such as CAS (Computer Aided Surgery) it is necessary to know the imaging properties for the C-arm X-ray system completely.

For applications in the field of tomosynthesis and computed tomography it is also necessary to know the exact imaging properties of the relevant X-ray apparatus for the reconstruction of the X-ray images.

Therefore, it is an object of the invention to provide a method and a device that enable correction of the distortions in the patient images.

This object is achieved according to the invention in that the X-ray examination apparatus includes at least one calibration member for forming a reference pattern and a correction unit for correcting distortions in X-ray images on the basis of the pattern of the calibration members actually formed in the patient X-ray image and the reference pattern.

SUMMARY OF THE INVENTION

The positions of the housing of the image intensifier and that of the X-ray source relative to a fixed system of space co-ordinates are determined by means of a position measuring device. To this end, reference sensors are mounted on the housings of the image intensifier and the X-ray source, each of said sensors defining a respective image intensifier system of co-ordinates and an X-ray source system of co-ordinates, which systems of coordinates are fixed relative to the relevant housing. Moreover, suitable calibration members are mounted on the image intensifier or on the X-ray source or on both. The position of these calibration members is fixed relative to the respective housing of the image intensifier or of the X-ray source, thus enabling the determination of the reference pattern associated with the calibration bodies relative to the relevant system of co-ordinates. To this end, the position of the calibration members is calculated in the system of co-ordinates formed by the position measuring device.

The calibration members have a fixed, known shape and appearance. They are reproduced and identified as actual patterns, together with the patient, in the patient X-ray image. The imaging properties of the X-ray examination apparatus can be determined on the basis of the known shape and appearance as well as the known position of the calibration members relative to the housings of the image intensifier and of the X-ray source in the calculated reference pattern and the position of the calibration members in the patient X-ray image. The determination of the imaging properties enables correction of distortions which are due, for example, to the curved surface of the image intensifier, to a change of the terrestrial magnetic field, or to bending of the C-arm.

It has also been found that it is also advantageous to measure the position of the calibration members directly by means of the position measuring device. This position is detected directly by means of suitable indicator means, provided with reference sensors, and is applied to the position measuring device by way of the reference sensors. The imaging properties of the X-ray apparatus are then calculated from the known position data of the calibration members and the positions of the calibration members reproduced notably at the edge in the patient X-ray images.

A patient X-ray image wherefrom distortions have been removed can thus be produced by means of a single patient X-ray exposure, without utilizing several calibration exposures or several patient X-ray exposures. The correction of the distortion is performed intra-operatively, so that a distortion-free X-ray image is presented to the observer.

It has been found that in a preferred embodiment of the invention the calibration members are advantageously provided, for example, in a circular pattern in a disc which is transparent to X-rays, said calibration members consisting of X-ray absorbing spheres or wires. The X-ray transparent disc, for example made of Plexiglas, does not absorb the X-rays so that the patient image is not additionally falsified thereby. Because of their high absorption, however, the spheres or wires can be recognized very well in the patient images.

These Plexiglas discs with the circular arrangement of the metal spheres or the crossed metal wires are arranged at a respective defined distance from and in front of the image intensifier and/or the X-ray source. The imaging properties of the X-ray examination apparatus can be determined on the basis of the shifts or differences between the positions of the calibration members in the calculated reference pattern and the pattern of the calibration members actually formed in the patient X-ray image, thus enabling correction of distortions in the patient X-ray image.

In the case of computed tomography (CT) a three-dimensional X-ray image is reconstructed from a plurality of slice images. Because external magnetic fields again act on the CT apparatus and shifts between the X-ray source and the detector have a negative effect on the patient X-ray image, knowledge of the imaging properties of the CT apparatus is necessary so as to reconstruct a distortion-free X-ray image. In this case the calibration members are arranged in such a manner that they are visible in each slice image and that the imaging properties of the CT apparatus can be determined by means of the calculated reference pattern of the calibration members and the pattern of the calibration members actually formed in the patient X-ray image.

In the case of tomosynthesis, also involving the acquisition of slice images, the correction of distortions in accordance with the invention can be performed by utilizing calibration members and determining the imaging properties.

BRIEF DESCRIPTION OF THE DRAWINGS

An embodiment will be described in detail hereinafter with reference to the drawings. Therein.

DESCRIPTION OF THE PREFERRED EMBODIMENTS

Figure 1:
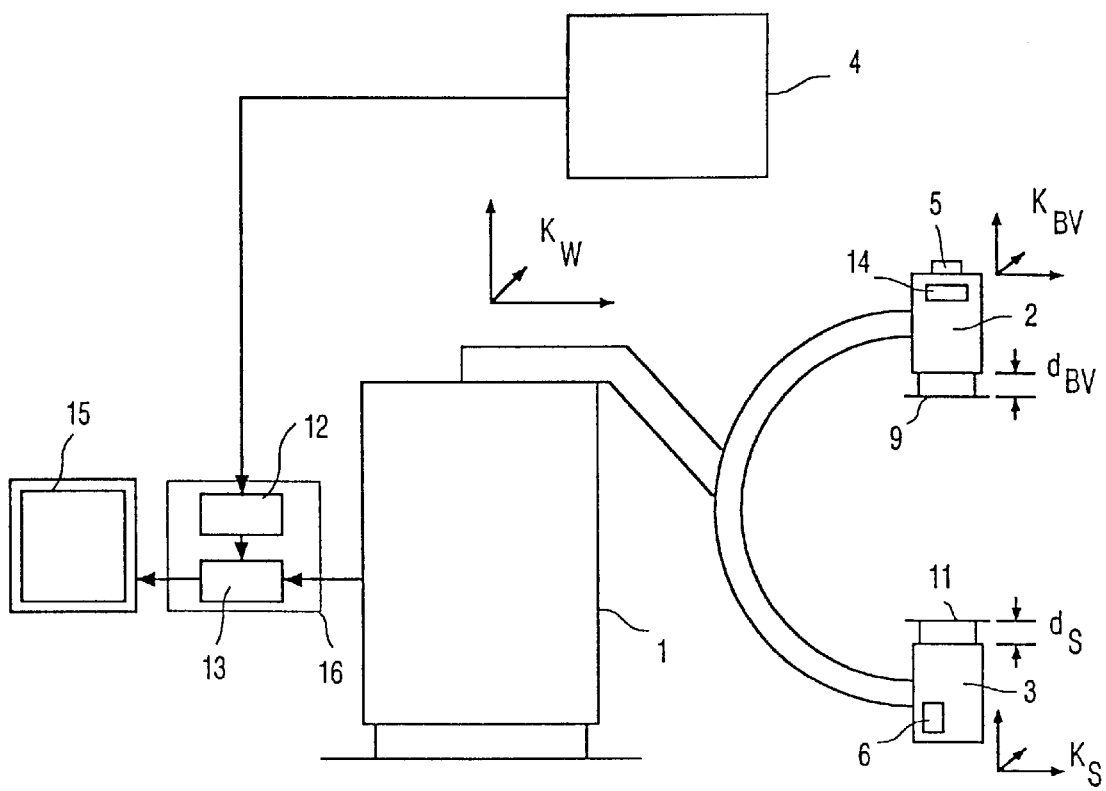
FIG. 1 shows diagrammatically a C-arm X-ray system.

The C-arm X-ray system shown in FIG. 1 includes a housing 1 for mounting the C-arm on which there are arranged an image intensifier 2 and an X-ray source 3. Reference sensors 5 are attached to the image intensifier 2; these reference sensors may be realized as LEDs, for example, in the case of an optical position measuring device 4. The reference sensors 5 apply the co-ordinates of the image intensifier housing 2 to the position measuring device 4. Reference sensors 6 are also mounted on the X-ray source 3; these reference sensors apply the co-ordinates of the X-ray source 3 to the position measuring device 4. The reference sensors 5 and 6 define a respective system of co-ordinates that is fixed relative to the respective housing (an image intensifier co-ordinate system $K_{BV}$ and an X-ray source co-ordinate system $K_S$) The position measuring device 4 forms a space co-ordinate system $K_W$ in which the position of the co-ordinate systems $K_{BV}$ and $K_S$ is known as a result of the transfer of the positions by way of the reference sensors 5 and 6. Calibration members 8 are arranged at a defined distance $d_{BV}$ from and in front of the opening in the image intensifier 2 which serves for the entry of the X-rays emitted by the X-ray source 3.

Figures 2, 3:
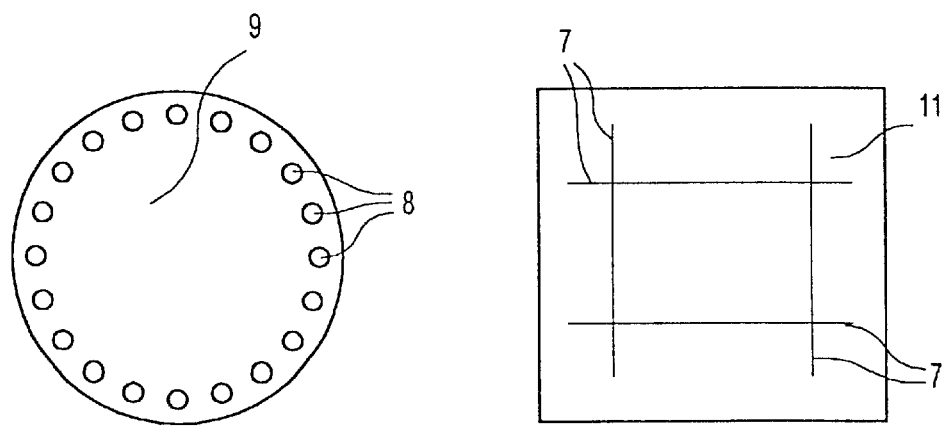
FIG. 2 shows calibration members of the image intensifier.
FIG. 3 shows calibration members on the X-ray source.
Figure 4:
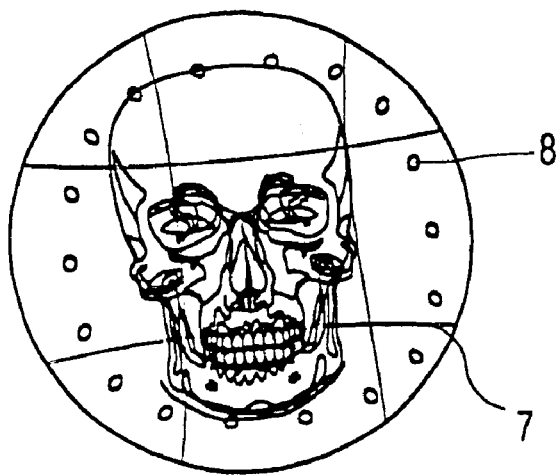
FIG. 4 shows a distorted patient X-ray image.
Figure 5:
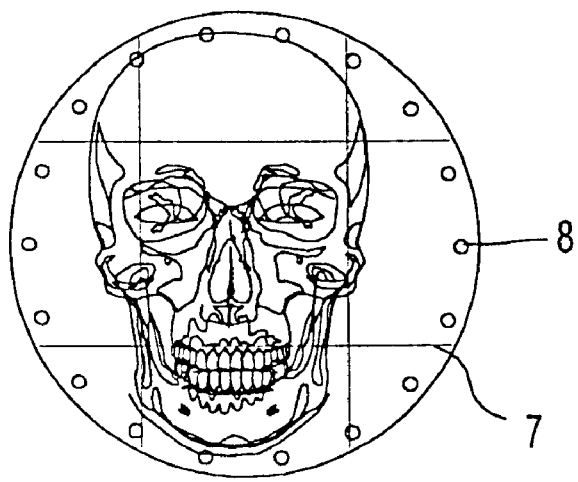
FIG. 5 shows a patient X-ray image wherefrom distortions have been removed.

The calibration members 8 are shown in FIG. 2 and are formed, for example by small metal spheres which are arranged in a circle at the edge of a transparent Plexiglas disc 9. At a defined distance $d_S$ from the X-ray source 3 there is provided a further transparent Plexiglas disc 11 with crossed metal wires which produce an X-ray shadow as calibration members 7 as shown in FIG. 3. Using the known distances $d_S$ and $d_{BV}$ and the known geometry of the calibration members 7 and 8 in the respective Plexiglas discs in front of the image intensifier 2 and in front of the X-ray source 3, respectively, the exact position of the calibration members can be determined relative to the image intensifier 2 or the X-ray source 3 and hence also for the relevant co-ordinate systems $K_{BV}$ and $K_S$. The X-ray source 3 and the image intensifier 2 are unambiguously localized in the space co-ordinate system $K_W$ by way of their associated co-ordinate systems $K_{BV}$ and $K_S$ and the position measuring device 4. The position measuring device 4 applies the positions of the calibration members 7 and 8 on the image intensifier 2 and the X-ray source 3 to an arithmetic unit 12 which is included in the image processing unit 16. The reference pattern is calculated therein. The image intensifier 2 includes a CCD camera 14 which picks up the X-rays converted into visible radiation. Subsequently, the patient X-ray image with the calibration members 7 and 8 reproduced therein is applied to the arithmetic unit 12. The imaging properties of the C-arm X-ray system can be determined on the basis of the positions of the calibration members 7 and 8 in the reference pattern and the positions of the calibration members 7 and 8 in the patient X-ray image; differences therebetween can be determined by comparison of the positions. Differences between the positions indicate distortions which are removed in the correction unit 13 while taking into account the calculated imaging properties. FIG. 4 shows a distorted patient X-ray image. The distortion-free image (FIG. 5) of the patient is displayed on the display unit 15.

The position of the calibration members can be detected directly by means of an indicator instrument that is not shown herein but is localized, by way of attached reference sensors, by the position measuring device 4.

In a further embodiment only the image intensifier 2 is measured by means of the position measuring device 4. The position of the image intensifier co-ordinate system $K_{BV}$ relative to the external co-ordinate system $K_W$ is thus known. In conjunction with the knowledge of the shape and the position of the calibration members 7 in the source coordinate system $K_S$, the position of the focal point of the X-ray source 3 in the image intensifier co-ordinate system $K_{BV}$ or in the external co-ordinate system $K_W$ can be calculated from the position of the calibration members 7 of the X-ray source 3 in the patient image. Distortions caused in the patient X-ray image by bending of the C-arm X-ray system can thus be corrected.

In a third embodiment only the X-ray source 3 is measured by means of the position measuring device 4. The position of the source co-ordinate system $K_S$ relative to the outer co-ordinate system $K_W$ is thus known. In conjunction with the knowledge of the shape and the position of the calibration members 8 in the image intensifier co-ordinate system $K_{BV}$, the position of the image intensifier 2 in the X-ray source co-ordinate system $K_S$ or in the external co-ordinate system $K_W$ can then be calculated from the position of the calibration members 8 of the image intensifier 2 in the patient X-ray image. Distortions in the patient X-ray image can thus be corrected again.

It has been found that it is advantageous to provide the X-ray source 3 and the image intensifier 2 both with calibration members 7 and 8 and both with reference sensors 5 and 6, so that both can be measured. When neither the position of the X-ray source 3 nor that of the image intensifier 2 can be determined, each time only the visible respective other housing of the X-ray source 3 or the image intensifier 2, provided with reference sensors, is used to determine the imaging properties of the C-arm. This situation frequently occurs when use optical position measuring devices are used.

In a further embodiment of the invention image processing methods are applied so as to remove the calibration members 7 and 8, also being reproduced in the patient images, from the patient X-ray images by reducing the field of view. The surgeon is thus presented a non-falsified image of the patient.

The reference sensors may also be realized as purely geometrically distinguishable shapes. In that case the position measuring device recognizes such shapes and determines their position.

The calibration members may be provided, additionally or exclusively, on the patient or on the operating table so that they are reproduced in the patient X-ray image. Because of the reference sensors provided on the calibration members, their position is known for the calculation of the imaging properties.

What is claimed is:

1. An X-ray examination apparatus including an image processing unit, comprising:

first and second calibration members constructed to be transparent to x-rays, in disc-form and arranged in an X-ray beam path of the x-ray examination apparatus;

a position measuring device for detecting a spatial relationship between the first and second calibration members, where the image processing unit forms a reference pattern based on said detected spatial relationship; and a correction unit for correcting distortions in an X-ray image having a patient image and the reference pattern on the basis of the reference pattern.

2. An X-ray examination apparatus comprising:

a first calibration member provided on an x-ray source;

a second calibration member provided on an x-ray image intensifier;

a position measuring device for measuring a position of said first and second calibration member as arranged on said X-ray source and said x-ray image intensifier, respectively;

an arithmetic unit for calculating a reference pattern from known dimensions of said X-ray examination apparatus and the measured positions of said first and second calibration members;

a correction unit for correcting distortions in an X-ray image having a patient image and the reference pattern on the basis of the reference pattern; and a display unit for displaying the X-ray image.

3. The X-ray examination apparatus as claimed in claim 2, wherein the positions of said first and said second calibration members are detectable by an indicator device and a plurality of reference sensors.

4. A method of forming distortion-free X-ray images, said method comprising:

providing first and second calibration members in a path of an x-ray beam at measured first and second respective positions;

calculating a reference pattern associated with the at least one of said first and second calibration members based on said measured first and second positions;

forming an X-ray image including a patient image and the reference pattern; and correcting distortions of the patient image on the basis of the reference pattern.

5. An X-ray examination apparatus for providing an X-ray image including a patient image, comprising:

a first calibration member for forming a first reference pattern in the X-ray image;

a second calibration member for forming a second reference pattern in the X-ray image; and a correction unit for correcting any distortions of the patent image in the X-ray image on a basis of a positional relationship of the first calibration member and the second calibration member.

6. A method of providing an X-ray image including a patient image without any distortions, said method comprising:

calculating a positional relationship of a first calibration member and a second calibration member;

forming the X-ray image including the patient image, a first reference pattern formed by the first calibration member, and a second reference pattern formed by the second calibration member; and correcting any distortions of the patent image in the X-ray image on a basis of the positional relationship of the first calibration member and the second calibration member.

* * * * *